United States Patent
Gordon et al.

(10) Patent No.: US 10,234,428 B2
(45) Date of Patent: Mar. 19, 2019

(54) LASER TWEEZER SYSTEM FOR MEASURING ACOUSTIC VIBRATIONS OF NANOPARTICLES

(71) Applicants: Reuven Gordon, Victoria (CA); Skyler Wheaton, Victoria (CA); Ryan M. Gelfand, Victoria (CA)

(72) Inventors: Reuven Gordon, Victoria (CA); Skyler Wheaton, Victoria (CA); Ryan M. Gelfand, Victoria (CA)

( * ) Notice: Subject to any disclaimer, the term of this patent is extended or adjusted under 35 U.S.C. 154(b) by 5 days.

(21) Appl. No.: 14/581,949

(22) Filed: Dec. 23, 2014

(65) Prior Publication Data

US 2015/0330951 A1 Nov. 19, 2015

Related U.S. Application Data

(60) Provisional application No. 61/992,831, filed on May 13, 2014.

(51) Int. Cl.
| | |
|---|---|
| *G01N 29/12* | (2006.01) |
| *G01N 29/24* | (2006.01) |
| *G01N 21/65* | (2006.01) |
| *G01N 15/10* | (2006.01) |
| *G01N 33/483* | (2006.01) |
| *G01N 33/487* | (2006.01) |
| *B01L 3/00* | (2006.01) |
| *G02B 21/32* | (2006.01) |

(Continued)

(52) U.S. Cl.
CPC ........ *G01N 29/12* (2013.01); *B01L 3/502761* (2013.01); *G01N 15/10* (2013.01); *G01N 21/63* (2013.01); *G01N 21/65* (2013.01); *G01N 29/2418* (2013.01); *G01N 33/4833* (2013.01); *G01N 33/48728* (2013.01); *G02B 21/32* (2013.01); *B01L 2200/0668* (2013.01); *B01L 2400/0454* (2013.01); *G01N 2015/0038* (2013.01); *G01N 2291/023* (2013.01)

(58) Field of Classification Search
CPC .... G01N 29/2418; G01N 29/12; G01N 21/63; G01N 21/35; G01N 21/64; G01N 21/65; G01N 21/658
USPC ............................................. 73/643; 356/301
See application file for complete search history.

(56) References Cited

U.S. PATENT DOCUMENTS

| | | | | |
|---|---|---|---|---|
| 4,127,329 A | * | 11/1978 | Chang ................. | G01J 3/44 356/301 |
| 5,469,255 A | * | 11/1995 | Kamada ............... | G01N 21/636 250/458.1 |

(Continued)

OTHER PUBLICATIONS

Pang et al., "Optical Trapping of 12 nm Dielectric Spheres Using Double-Nanoholes in a Gold Film", American Chemical Society Publication, Aug. 12, 2011.*

(Continued)

*Primary Examiner* — Helen C Kwok
(74) *Attorney, Agent, or Firm* — Klarquist Sparkman, LLP

(57) ABSTRACT

Optically trapped specimens (typically nanoparticles having diameters between 1 and 50 nm) are excited with an optical beam so as to induce vibrations in the specimens. A trapping optical beam and the excitation optical beam can produce vibrations based on a difference frequency based on the trapping optical beam and the excitation optical beam. Scattered optical radiation as a function of modulation frequency can be recorded and used to identify or characterize the specimen.

25 Claims, 8 Drawing Sheets

(51) Int. Cl.
*G01N 21/63* (2006.01)
*G01N 15/00* (2006.01)

(56) References Cited

U.S. PATENT DOCUMENTS

| | | | | |
|---|---|---|---|---|
| 5,674,743 | A * | 10/1997 | Ulmer | B01J 19/0046 422/82.08 |
| 5,679,950 | A * | 10/1997 | Baba | G01N 21/6404 250/281 |
| 5,949,532 | A * | 9/1999 | Schrof | G01J 3/44 250/458.1 |
| 6,388,246 | B1 * | 5/2002 | Fry | G01S 7/487 250/221 |
| 6,399,397 | B1 * | 6/2002 | Zarling | B82Y 15/00 435/7.1 |
| 6,489,609 | B1 * | 12/2002 | Baba | H01J 49/42 250/281 |
| 6,911,646 | B1 * | 6/2005 | Weitekamp | B82Y 20/00 250/225 |
| 7,515,269 | B1 * | 4/2009 | Alexander | G01N 21/658 356/445 |
| 8,057,655 | B1 * | 11/2011 | Cohen | B03C 5/026 204/450 |
| 8,491,454 | B2 * | 7/2013 | Wong | G01N 33/54313 422/400 |
| 8,618,510 | B2 * | 12/2013 | Palmer | G01N 15/1436 250/251 |
| 9,443,631 | B1 * | 9/2016 | Pan | G02B 27/0018 |
| 2003/0158474 | A1 * | 8/2003 | Scherer | B82Y 15/00 600/409 |
| 2004/0012778 | A1 * | 1/2004 | Li | G01N 21/658 356/301 |
| 2005/0187438 | A1 * | 8/2005 | Xie | A61B 5/14532 600/310 |
| 2005/0221333 | A1 * | 10/2005 | Sundararajan | C12Q 1/6827 435/6.19 |
| 2006/0232775 | A1 * | 10/2006 | Hairston | G01J 3/02 356/388 |
| 2006/0243897 | A1 * | 11/2006 | Wang | G21K 1/006 250/251 |
| 2007/0084727 | A1 * | 4/2007 | Cummings | B82Y 15/00 204/451 |
| 2008/0239307 | A1 * | 10/2008 | Talley | G01J 3/02 356/301 |
| 2009/0180121 | A1 * | 7/2009 | Ichinose | G01N 15/0255 356/441 |
| 2009/0323732 | A1 * | 12/2009 | Benabid | H01S 3/305 372/3 |
| 2010/0014078 | A1 * | 1/2010 | Dholakia | G01J 3/28 356/301 |
| 2010/0128275 | A1 * | 5/2010 | Chau | B82Y 15/00 356/445 |
| 2010/0141940 | A1 * | 6/2010 | Caro | G01N 15/1459 356/301 |
| 2010/0241357 | A1 * | 9/2010 | Chan | G01J 3/44 702/19 |
| 2010/0245816 | A1 * | 9/2010 | Shen | B82Y 20/00 356/301 |
| 2011/0249259 | A1 * | 10/2011 | Van Dorpe | B82Y 15/00 356/301 |
| 2012/0241643 | A1 * | 9/2012 | Palmer | G01N 15/1436 250/428 |
| 2013/0171685 | A1 * | 7/2013 | Schutze | G01N 15/1468 435/34 |
| 2014/0004559 | A1 * | 1/2014 | Hill | G01N 21/01 435/34 |
| 2014/0045277 | A1 * | 2/2014 | Gordon | G01N 33/566 436/501 |
| 2014/0150534 | A1 * | 6/2014 | Dennin | G01N 11/00 73/54.01 |
| 2014/0185042 | A1 * | 7/2014 | Baets | G01N 21/658 356/301 |
| 2014/0204372 | A1 * | 7/2014 | Pang | G01N 21/658 356/301 |
| 2014/0320849 | A1 * | 10/2014 | Chou | B03C 5/026 356/72 |
| 2014/0374581 | A1 * | 12/2014 | Dionne | G21K 1/006 250/251 |

OTHER PUBLICATIONS

Ivanda et al., "Raman scattering of acoustical modes of silicon nanoparticles embedded in silica matrix," *J. Raman Spectroscopy*, 37:161-165 (2006).

Pang and Gordon, "Optical trapping of a single protein," *Nano Letters*, 12(1):402-406 (2012).

Pang and Gordon, "Optical trapping of 12 nm dielectric spheres using double-nanoholes in a gold film," Supplemental Information, 3 pages (2012).

* cited by examiner

LASER TWEEZER SYSTEM FOR MEASURING ACOUSTIC VIBRATIONS OF NANOPARTICLES

CROSS REFERENCE TO RELATED APPLICATION

This application claims the benefit of U.S. Provisional Application No. 61/992,831, filed May 13, 2014, which is hereby incorporated by reference in its entirety.

BACKGROUND

Optical tweezers have been used to trap nanoscale dielectric particles using forces applied with focused laser beams. An electric field gradient at the beam waist draws particles to the center of the beam. Particles also experience a force in the direction of beam propagation, and thus tend to be situated slightly displaced from the beam waist along the direction of propagation. While conventional optical tweezers are useful in many applications, improvements are needed to expand the range of available applications, particularly for trapping particles <50 nm in size.

SUMMARY

In the examples discussed below, high frequency optical excitation is applied so that trapped samples are heated. Motion from heated samples is detected based on elastic scattering of light that can be detected at much lower frequencies than actual specimen vibration frequencies. Some methods comprise optically trapping a sample and applying an excitation optical signal to the optically trapped sample so as to excite a vibration of the optically trapped sample. A portion of the excitation optical signal received from the sample (or a portion of another optical signal) is detected so as to determine a vibrational frequency associated with the sample. In alternative examples, the sample is optically trapped in response to the applied excitation signal, in response to a trapping optical signal, or in response to a combination of the excitation optical signal and the trapping optical signal. In typical examples, the sample is optically trapped at or near an aperture, wherein the aperture is a single nanohole or a double nanohole having an effective trapping region diameter between 0.1 and 300 nm. According to some embodiments, the aperture can have one or more cusps. In some cases, the aperture is defined in a metallic film. In a particular example, the excitation optical signal includes first and second optical signals, and the vibration of the sample is excited in response to a frequency difference between the first and second optical signals. Typically, the frequency difference is a heterodyne frequency between the first and second optical signals. The excitation optical signal can be produced by one or two semiconductor lasers (external cavity, distributed feedback, VCSEL or distributed Bragg reflector lasers), solid state lasers, a dye laser, or a mode-locked laser. In most cases, two lasers of any kind can used to produce a heterodyne frequency. A single mode-locked laser can also be used to induce specimen vibrations. With a pulsed laser, a pump-probe setup can be used, which either has a probe beam from a CW laser or from the pulsed laser itself as a beam portion that is split from the main beam.

Apparatus comprise an excitation optical radiation source that delivers an excitation optical beam to an optically trapped specimen. A control system is coupled to the optical radiation source so as to select a modulation frequency associated with the excitation optical beam. A detector is situated to receive at least a portion of the excitation optical beam responsive to vibrations induced in the trapped specimen by the excitation optical beam. Typically, a detection signal is produced that is associated with the magnitude of the induced vibrations. Modulation frequencies that are at or near specimen resonance frequencies tend to produce larger detection signals due to the increase of vibrational amplitudes at such modulation frequencies. In some examples, the control system selects a plurality of modulation frequencies and the detector provides a detection signal corresponding to the plurality of modulation frequencies. Typically, the control system selects the plurality of modulation frequencies by sweeping the modulation frequency in a frequency range. According to representative examples, the optical excitation source comprises a first optical source and a second optical source, and the control system adjusts a frequency of at least the first optical source and the second optical source to establish a heterodyne frequency, wherein the modulation frequency corresponds to the heterodyne frequency. The first optical source and the second optical source can be semiconductor lasers such as distributed feedback lasers, vertical cavity surface emitting lasers (VCSELs), solid state lasers, gas lasers, or other lasers that can provide pulsed or continuous wave outputs, including mode-locked pulses. In addition, external cavity semiconductor lasers (including Littman and Littrow configurations) can be used.

In some alternatives, a trapping optical radiation source applies a trapping optical beam to the sample, wherein the trapping and excitation optical radiation sources includes respective lasers and the control system is coupled so as to select the modulation frequency as a heterodyne frequency between the trapping optical beam and the excitation optical beam. In other examples, at least one nanohole, is situated so that the trapping optical beam is directed toward the nanohole so as to trap the specimen at the nanohole. The at least one nanohole can be a double nanohole. In further examples, the detector is situated to receive at least a portion of the excitation optical beam inelastically or elastically scattered by the trapped specimen.

These and other features and aspects of the disclosed technology are set forth below with reference to the accompanying drawings.

DETAILED DESCRIPTION

Figure 1:
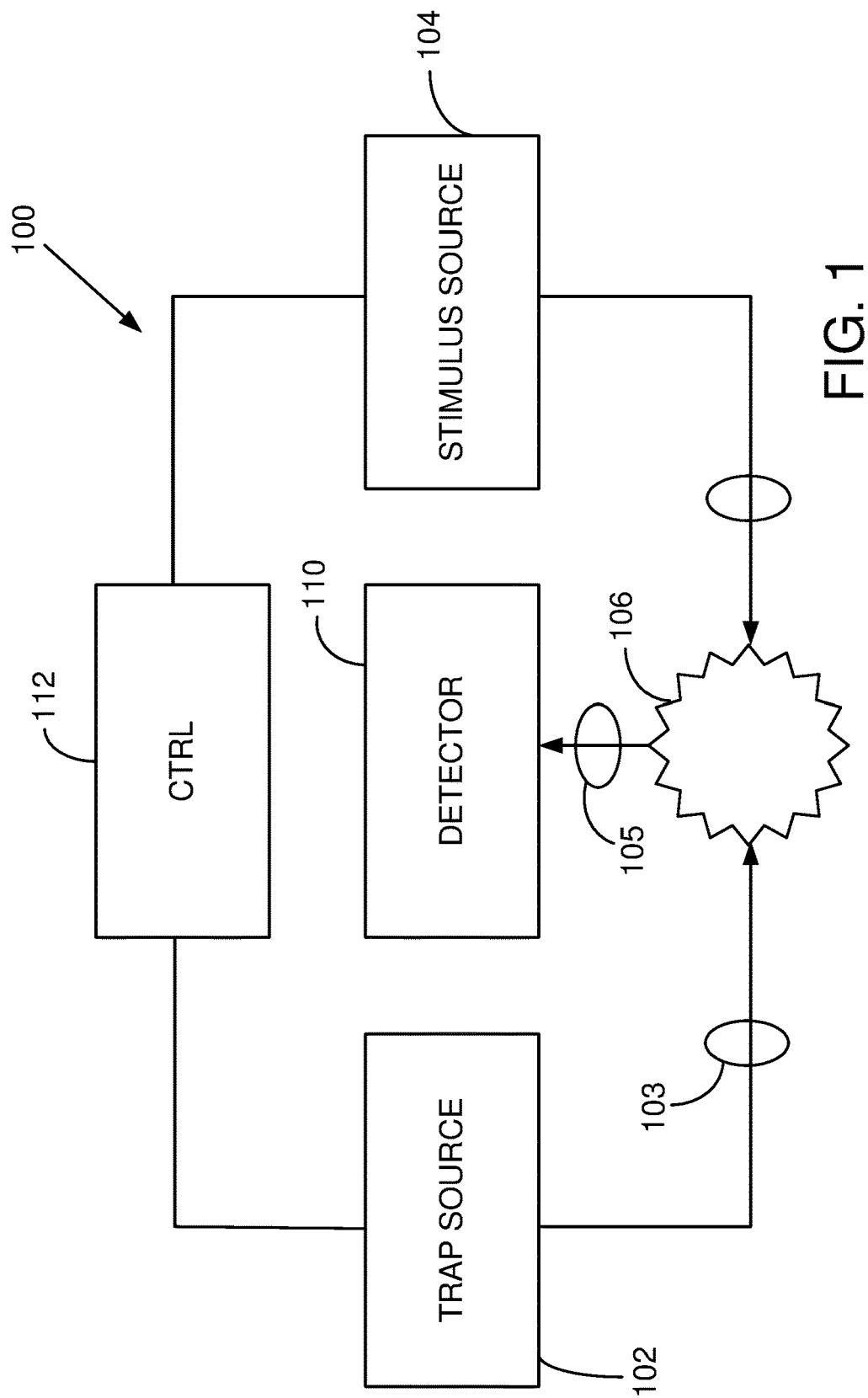
FIG. 1 is a schematic diagram of a system that optically traps a specimen, and applies an excitation or stimulus beam to produce vibrations of the specimen or a portion thereof.

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items.

The systems, apparatus, and methods described herein should not be construed as limiting in any way. Instead, the present disclosure is directed toward all novel and non-obvious features and aspects of the various disclosed embodiments, alone and in various combinations and subcombinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In some examples, values, procedures, or apparatus' are referred to as "lowest", "best", "minimum," or the like. It will be appreciated that such descriptions are intended to indicate that a selection among many used functional alternatives can be made, and such selections need not be better, smaller, or otherwise preferable to other selections.

The interaction of light with mechanical vibrations has had broad impact ranging from cavity optomechanics of micron structures (<10 GHz) to infrared and Raman spectroscopy of molecular vibrations (>3 THz). Between these frequency extremes is the so-called "terahertz gap" in which new approaches are needed to efficiently probe the vibrations of nanoparticles such as colloidal particles, quantum dots, proteins, DNA, and virions. Disclosed herein are methods and apparatus than can be applied to probing vibrations of nanoparticles using laser tweezers. The disclosed approaches can be used with single molecules, and thus can be applied to ultra-sensitive spectroscopy and detection applications. One or more optical beams are used to induce vibrations in a trapped specimen, and one or more beams (the same or different beams than the stimulus beams or a trapping beam) are directed to the specimen to detect vibrations. High frequencies are needed to induce high amplitude vibrations due to the high resonance frequencies of typical specimens. These induced high frequency variations can be detected at low frequencies based on scattered portions of optical beams. High frequency detection is not required. Thus, scattered portions of optical beams measured at low frequencies can be used to detect trapped specimen resonance frequencies of many GHz or THz.

A representative system 100 is shown in FIG. 1. A source 102 produces optical radiation that is directed to a specimen 106 via beam forming optics 103 so as to trap the specimen. A second source 104 directs a stimulus beam to the specimen 106. A detector 110 receives optical radiation from the source as collected by receiver optics 105 and produces a signal that varies based on the specimen's response to the optical radiation from the stimulus source. A controller 112 is coupled to the trap source 102 and the stimulus source 104 so as to control trapping and the frequency associated with one or both of the trapping and stimulus optical radiation. In some cases, the controller 112 produces a variable frequency, and the detector signal is recorded as a function of the variable frequency. For example, the controller 112 can adjust the frequencies of the stimulus optical radiation so as to produce a variable heterodyne frequency based on interference. The detector 110 can be coupled to a display to show detector signal or signal variations as a function of frequency, or the detector signal can be recorded for analysis or transmission.

Figure 2:
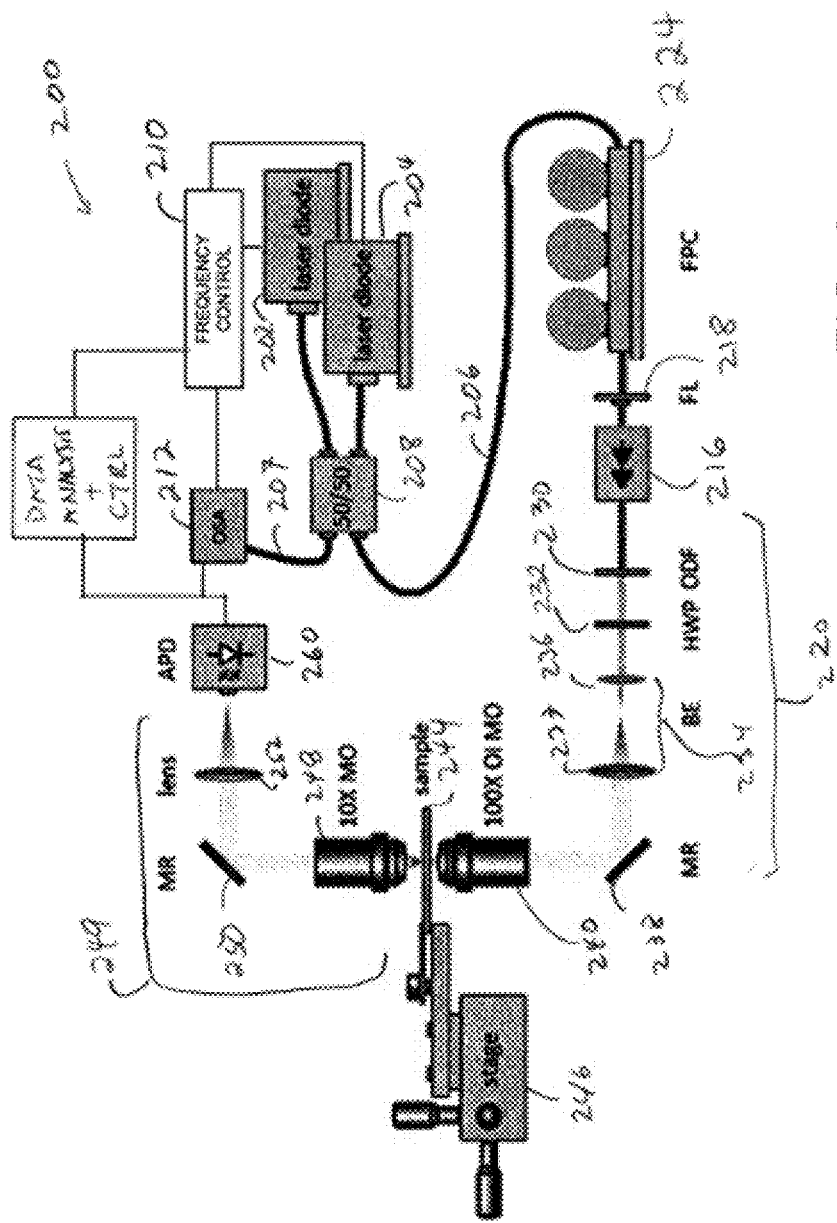
FIG. 2 is a schematic diagram of an optical trapping/excitation system based on an inverted microscope configuration.

Another example system 200 is shown in FIG. 2. First and second distributed feedback lasers (DFB lasers) 202, 204 produce first and second optical beams that are coupled into fibers 206, 207 (typically single mode fiber) connected to a polarization maintaining 50/50 coupler 208. Other types of beam combiners and coupling ratios other than 50/50 can be used. The optical beams of the lasers 202, 204 are at optical frequencies that can be tuned by adjusting laser temperature, drive current, or other parameters. As shown in FIG. 2, the fiber 207 delivers a portion of the combined beams to an optical spectrum analyzer (OSA) 212 to measure the frequency difference between the lasers 202, 204. A temperature controller 210 (or other frequency controller) is coupled to one or both of the lasers 202, 204 to adjust laser temperature so as to tune emission frequency of one or both of the lasers 202, 204 to establish a selected heterodyne frequency. In typical examples, the frequency difference between the lasers 202, 204 is varied so as to induce vibrations in a sample under investigation.

Lasers such as gas or solid state lasers can be used, but semiconductor lasers are convenient. DFB lasers are generally selected due to their relatively narrow spectral bandwidths. Laser output power and frequency can be severely affected by back reflections, and as shown in FIG. 2, an isolator 216 is placed between fiber launch (FL) optics 218 and beam forming/delivery optics 220, shown in the inverted microscope arrangement. A fiber polarization controller (FPC) 224 is used to align the polarization of the optical beams from the lasers 202, 204 before passing through the isolator 216 to minimize, reduce, or otherwise control back reflections. In the example of FIG. 2, the beam forming/delivery optics includes an attenuating optical filter 230, a half-wave plate 232, a beam expander 234 that includes lenses 236, 237, a turning mirror 238, and an objective lens 240 (shown as a 100× oil-immersion microscope objective) that focuses the combined beams into a sample secured to a specimen holder 244. A stage 246 retains the sample, and permits translation of the specimen holder 244 with the beam in transverse and longitudinal directions.

The combined beams or scattered optical radiation associated with one or more of the beams are directed through the specimen holder 244 to a receiver optical system 249 that includes first a condenser lens 248, a mirror 250, and a second condenser lens 252. The receiver optical system 249 directs the combined beams to a detector 260 such as an avalanche photodiode.

The specimen holder 244 includes a double-nanohole (DNH) aperture as a trapping site. DNHs are described in detail in Y. Pang and R. Gordon, "Optical trapping of a single protein," Nano Letters, 12(1), 402-406 (2012), which is incorporated herein by reference. Changes in transmission through the DNH are measured as voltage changes at the detector 260. These changes are actuated by a nanoparticle trapped in the DNH, as the traps are sensitive to dielectric loading. Interference between the optical beams of the first and second lasers 202, 204 leads to modulation of a local intensity at the DNH. This modulation occurs at a difference frequency (a heterodyne or beat frequency) between the two lasers. By tuning the frequency difference, a wide range of beat frequencies in the ~10 GHz-10 THz range can be obtained. This modulated intensity also modulates the electrostriction force (elongation of a particle under an applied field), and this vibrates the molecule. There is an increase in detector signal fluctuations when the beat frequency matches or approaches a vibrational resonance of the nanoparticle, corresponding to increases in particle motion so as to heat the particle by applying a modulation that matches the vibrational resonance.

Figure 3:
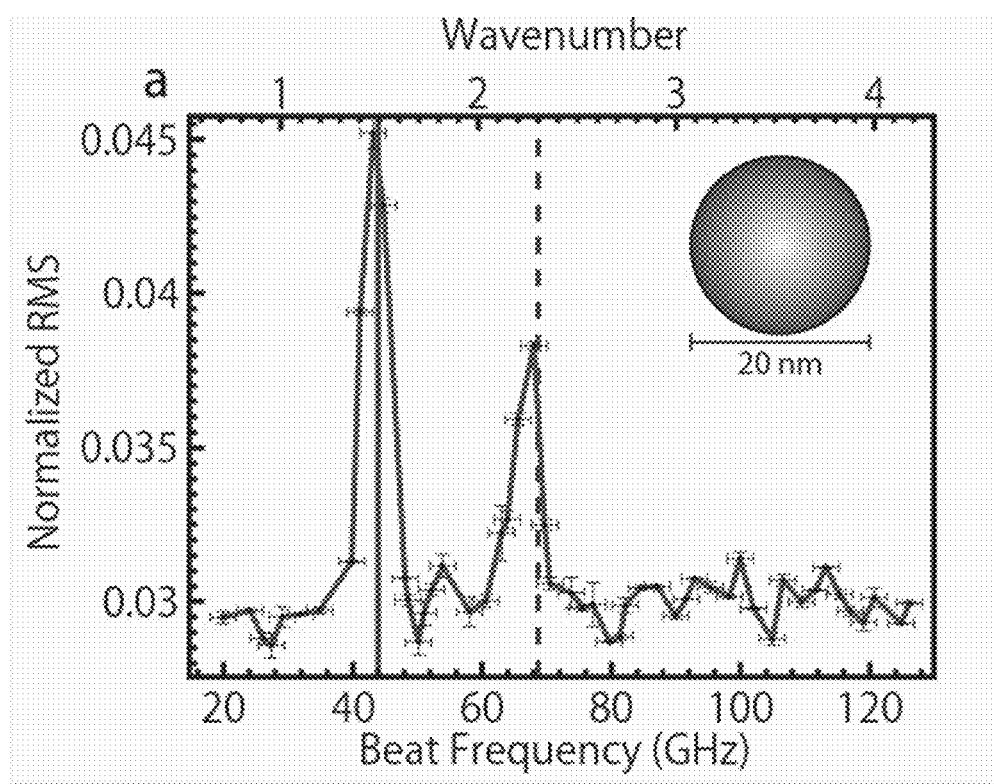
FIG. 3 is a graph of root mean squared (RMS) variation in photodetector signal for a trapped 20 nm diameter polystyrene particle as a function of beam frequency difference in GHz and wavenumber. The inset illustrates specimen structure. Standard Lamb theory for the vibrational resonances of a sphere predicts the l=2 peak at ~44.0 GHz, as shown. The peak at about 68.1 GHz can be associated with the l=0 order acoustic mode of the same sphere.

FIG. 3 is a plot of root mean squared (RMS) variation in detector signal for a trapped 20 nm diameter polystyrene particle as a function of beat frequency. Standard theory for the vibrational resonances of a sphere predicts a peak at ~44.0 GHz, as seen here. The other peak has been attributed to the lowest order acoustic mode in Raman experiments on smaller nanoparticles. Expected l=2 resonance of 20 nm diameter polystyrene spheres in vacuum (higher frequency) and in water (lower frequency) are noted with vertical lines. Note, those Raman measurements have lower resolution, can only probe higher frequencies, do not probe single particles and require complex and expensive spectroscopy systems—such as triple monochromators. Other methods to measure such peaks include Brillouin scattering, but Brillouin scattering based approaches are unable to probe single particles having sizes that are less than about 200 nm. Still other approaches are based on the Optical Kerr Effect, but such approaches have only been able to probe vibrations of strongly scattering (i.e., plasmonic) single nanoparticles, or of many particles in solution.

Figure 4:
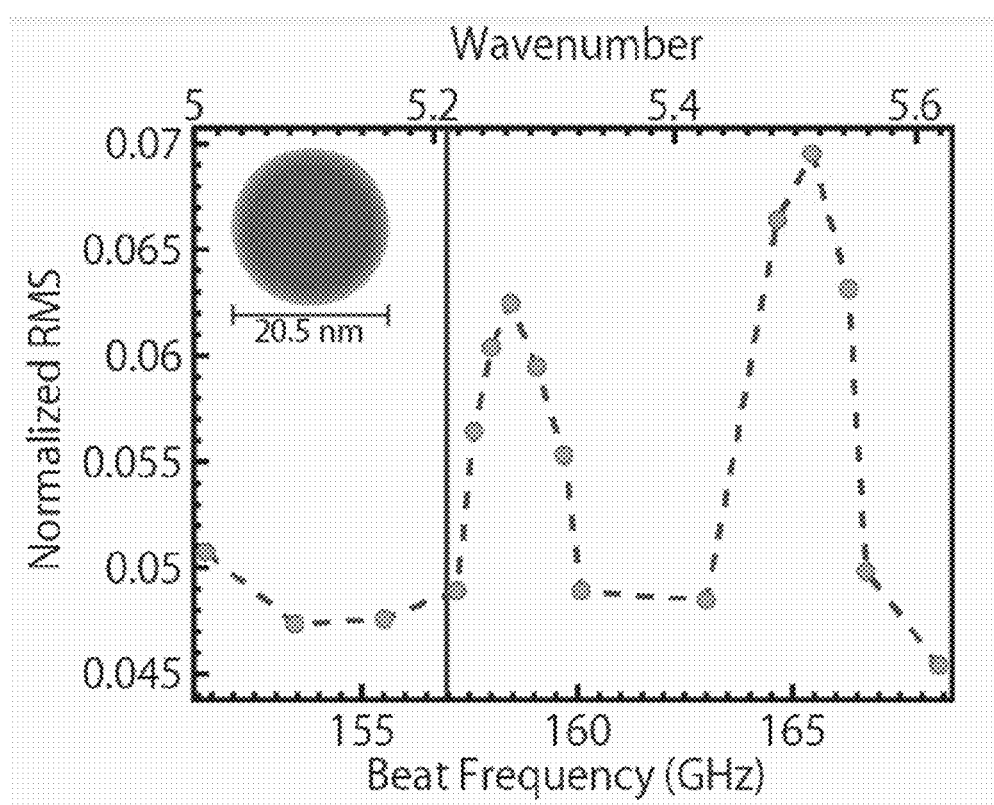
FIG. 4 is a graph of root mean squared (RMS) variation in photodetector signal for trapped titania spheres having a diameter of 20.5 nm showing similar peaks to those in FIG. 3, but at a much higher wavelength detuning (beat frequency). The inset illustrates specimen structure. The two peaks correspond to the material anisotropy of the titania, which demonstrates the applicability to measure anisotropy properties.
Figures 5A, 5B, 5C, 5D, 5E:
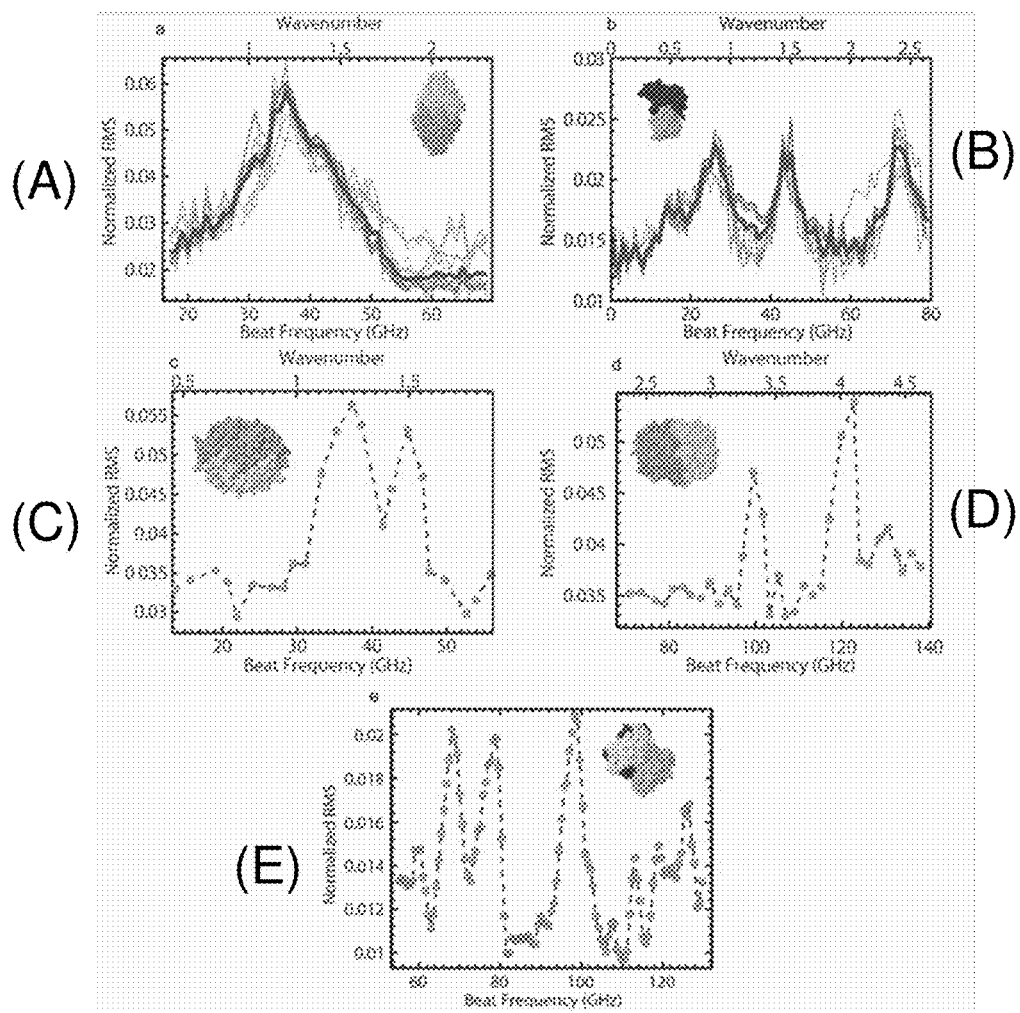
FIGS. 5A-E are graphs similar to those of FIGS. 3-4 obtained based on trapping of carbonic anhydrase, conalbumin, aprotinin, cyclooxygenase-2, and streptavidin, respectively. The insets illustrate specimen structures.

Titania spheres of 20.5 nm diameter show a similar peak, but at a much higher wavelength detuning (beat frequency) as shown in FIG. 4. The two peaks are attributed to one of two possible factors: the slightly ellipsoid nature of titania nanoparticles, or the crystal structure of titania particles leading to elastic anisotropy (the latter being the most likely explanation since it agrees well with the elastic anisotropy values in the literature). The value of the detuning is in the range expected for that size of titania particle. Based on these measurements, it is clear that a type of particle can be identified, and combined with other factors, such as the step height at trapping or the RMS roll off frequency, particle size can be assessed or estimated. Expected resonances of 21 nm diameter titania particles are at about 157 GHz and 161 GHz. FIGS. 5A-E are graphs similar to those of FIGS. 3-4 obtained based on trapping of carbonic anhydrase, conalbumin, aprotinin, cyclooxygenase-2, and streptavidin, respectively. Referring to FIG. 5D, the two peaks are attributed to the ellipsoidal nature of cyclooxygenase.

Figure 6:
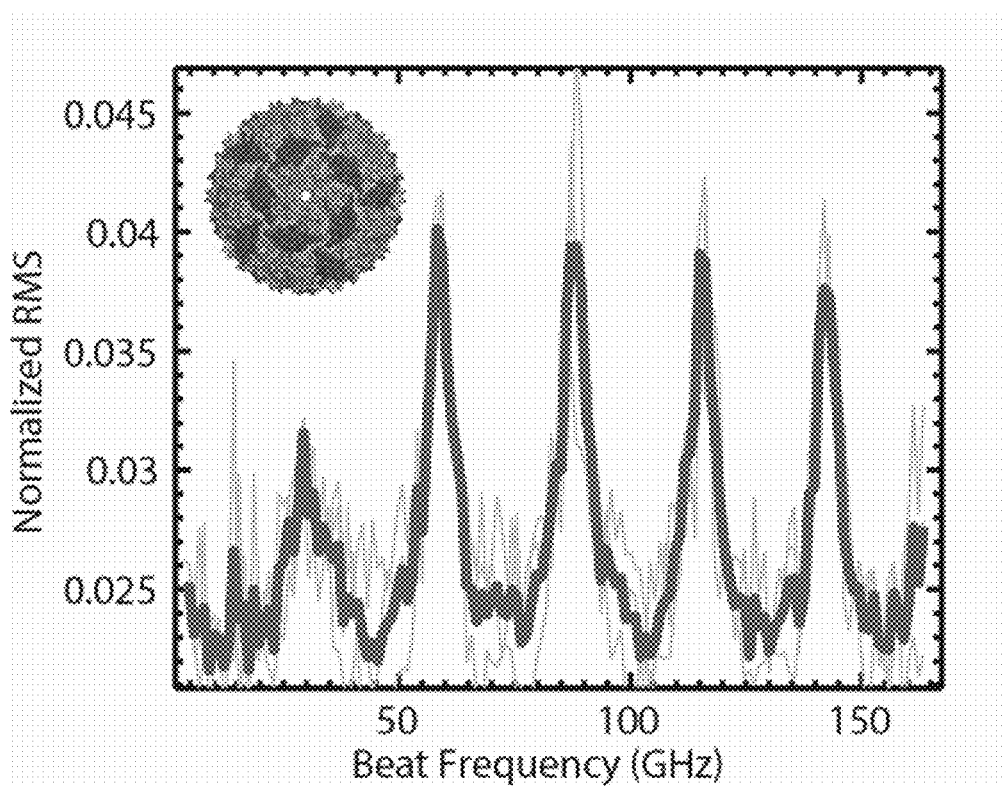
FIG. 6 is a graph of root mean squared (RMS) variation in photodetector signal obtained from the bacteriophage (bacteria virus) MS2. The inset shows the capsid structure (about 27.5 nm across).

Similar approaches can be used for the investigation, manipulation, and identification of DNA (e.g. for sequencing), viruses (e.g., for detection, noting heterogeneity, etc.), colloids (e.g. for measuring polydispersity), protein complexes (e.g., for measuring binding affinities), antibodies (e.g. for controlling antibody synthesis) and other applications. FIG. 6 is a graph of root mean squared (RMS) variation in photodetector signal obtained from the bacteriophage (bacteria virus) MS2.

Figure 7A:
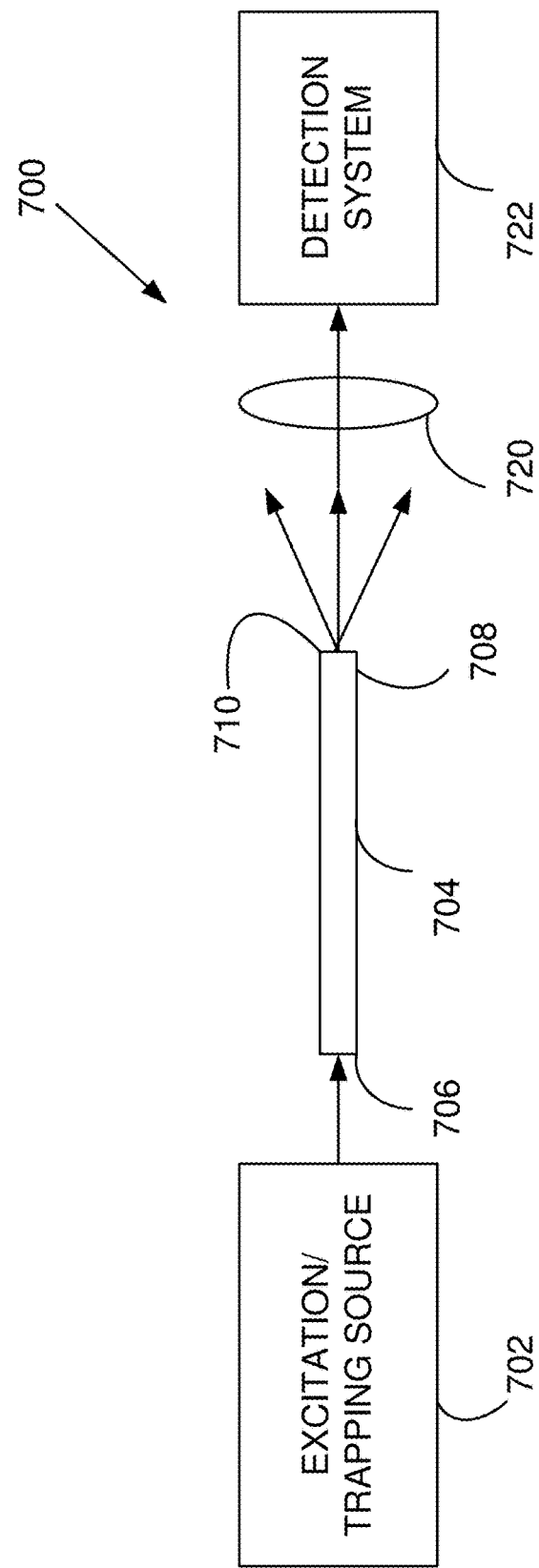
FIGS. 7A-7B illustrate a representative fiber-based system having a nano-aperture situated at a fiber output surface.
Figure 7B:
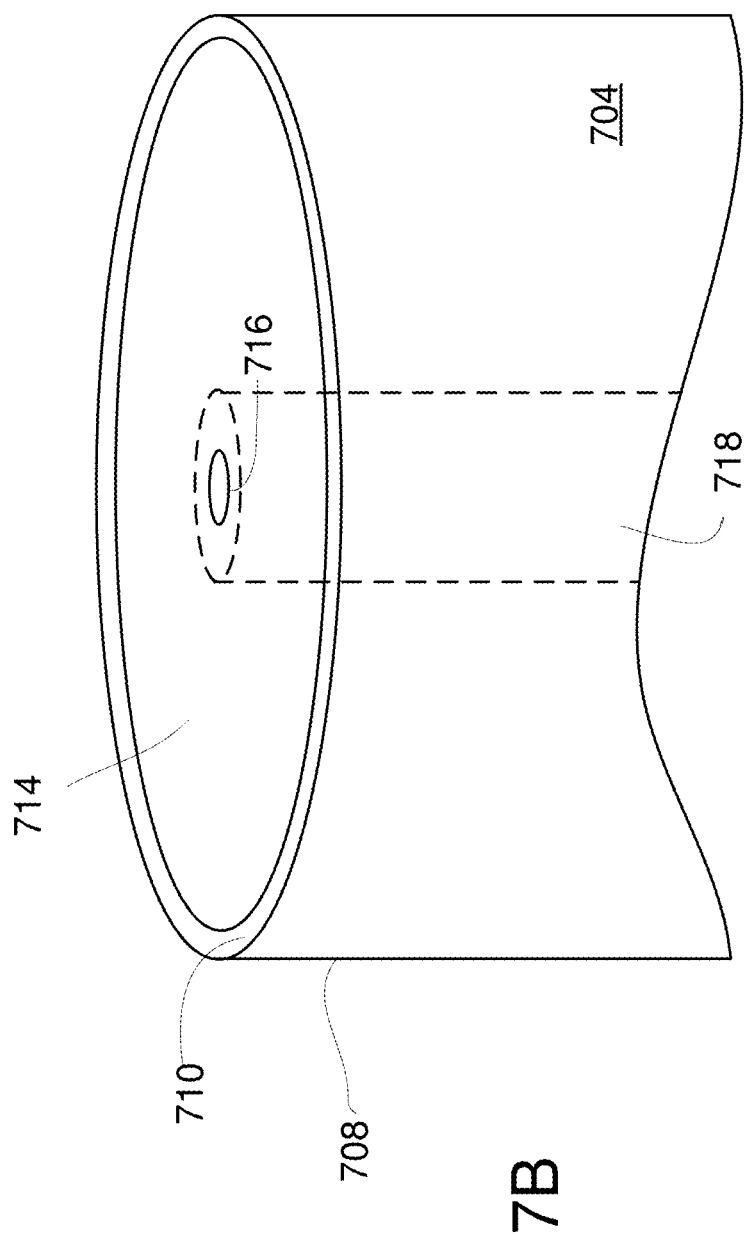

Referring to FIGS. 7A-7B, a representative fiber-based system 700 includes an optical excitation and/or trapping source 702 that delivers an excitation or trapping optical beam to a beam input end 706 of an optical fiber 704 or other optical waveguide. The beam (or beams) are guided to a beam output surface 710 at a beam output end 708. The output surface 710 includes a nano-aperture 716 defined in a metallic layer 714 situated on the output surface 710. The nano-aperture 716 is situated at the core region 718 of the optical fiber 704, and is shown in FIG. 7B as centered on the fiber core, but other locations can be used. A detection system 722 receives optical radiation responsive to the optical excitation beam and collected by receiver optics 720 from a specimen situated at the nano-aperture 716. Typically, the received optical radiation is associated with increased specimen vibration induced by the excitation optical beam.

REPRESENTATIVE EXAMPLES

Examples of the disclosed technology include a laser tweezer system that traps nanoparticles (e.g., colloidal particles, quantum dots, DNA, proteins, viruses, etc.) and uses a modulated laser source to excite the vibrations of the trapped nanoparticles and probe these vibrations. In some cases, the tweezer laser is also the modulated laser or is separate from the modulated laser. The modulation can be obtained by interfering two laser beams of different frequencies. The lasers can be distributed feedback lasers operating at wavelengths from 500 nm to 2 µm. In other examples, the two lasers are VCSEL. One or more of the lasers can be an external cavity laser, a Ti:Sapphire CW laser, a dye laser, or a mode locked laser (e.g., Ti:Sapphire). In some embodiments, the laser tweezer system uses an inverted microscope setup. In particular examples, the laser tweezer system uses an aperture in a metal film for trapping, and in some examples, the aperture is a double nanohole, or similar shape with cusps to enhance trapping of nanoparticles in the 0.1 nm to 50 nm range. Fibers can be used to deliver beams to and from the specimen, and the aperture can be integrated on the end of a fiber coated with a metal. In typical examples, the vibrational resonances of the nanoparticles lead to increased motion of the particle when the laser is at or near a resonance frequency and this can be detected in the optical radiation scattered by the particle, as detected with a photodiode (or avalanche photodiode or other optical detector). In some cases, light scattering shows the vibrational resonance by heating the particle, resulting in increased Brownian motion. Alternatively, light scattering can be associated with a vibrational resonance related to particle polarizability. In some examples, a spectrometer (or other optical spectrum analyzer) is used to monitor the wavelengths of the lasers and/or the wavelength of the inelastically scattered photons (such as a Raman signal) that shows the vibrational resonance. In typical applications, nanoparticles are identified based on, for example, size or composition, or on dynamic changes in their state (e.g., protein binding). Other applications include DNA sequencing or the evaluation of DNA-protein interactions, viruses (virions), virus interactions, protein-small molecule interactions, protein-peptide interactions, protein-protein interactions (including with antibodies), macromolecules and macromolecular interactions, colloidal particle analysis, so as to measure material properties and polydispersity.

Having described and illustrated the principles of the disclosed technology with reference to the illustrated embodiments, it will be recognized that the illustrated embodiments can be modified in arrangement and detail without departing from such principles. The particular arrangements above are provided for convenient illustration, and other arrangements can be used, and we claim all that is encompassed by the appended claims.

We claim:

1. A method, comprising:
   optically trapping at least one sample particle;
   applying an excitation optical signal at an excitation frequency to the optically trapped sample particle so as to excite a vibrational resonance of the optically trapped sample particle associated with an electrostriction force, wherein the excitation optical signal includes first and second optical signals at respective frequencies and the excitation frequency is a heterodyne frequency associated with a difference between wavelengths of the first and second optical signals and the vibration of the sample particle is excited in response to the heterodyne frequency; and
   detecting a portion of the excitation optical signal at the heterodyne frequency received from the sample particle due to elastic scattering so as to determine a vibrational frequency associated with vibration of the sample particle, wherein the determined vibrational frequency of the optically trapped sample particle is based on sample particle shape, size, and elastic properties.

2. The method of claim 1, wherein the sample particle is optically trapped in response to the applied excitation optical signal.

3. The method of claim 1, wherein the sample particle is optically trapped in response to a trapping optical signal.

4. The method of claim 1, wherein the sample particle is optically trapped in response to a trapping optical signal and the excitation optical signal.

5. The method of claim 1, further comprising optical trapping of the sample particle in an aperture.

6. The method of claim 5, wherein the aperture is a double nanohole having an effective trapping region diameter of between 0.1 nm and 50 nm.

7. The method of claim 5, wherein the aperture has cusps.

8. The method of claim 5, wherein the aperture is defined in a metallic film.

9. The method of claim 1, further comprising:
   tuning the heterodyne frequency over a frequency range; and
   detecting portions of the excitation optical signal at a plurality of heterodyne frequencies in the frequency range.

10. The method of claim 9, wherein the frequency range is 10 GHz to 10 THz.

11. The method of claim 1, wherein the excitation optical signal is produced with at least one semiconductor laser, solid state laser, dye laser, or mode-locked laser.

12. The method of claim 1, wherein the sample particle comprises one or more of DNA, a virus, a colloid, a protein complex, an antibody, or a macromolecule.

13. An apparatus, comprising:
   a vibration inducing optical radiation source that delivers a modulated excitation optical beam to an optically trapped specimen, wherein the optical radiation source comprises a first optical source and a second optical source, and the control system adjusts a frequency of at least one of the first optical source and the second optical source to establish a heterodyne frequency, wherein the modulation frequency corresponds to the heterodyne frequency;
   a control system coupled to the optical radiation source so as to select a modulation frequency associated with the modulated excitation optical beam to excite a vibrational resonance of the optically trapped specimen under an electrostriction force; and
   a detector situated to receive at least a portion of the modulated excitation optical beam at the selected modulation frequency as modulated by the vibration of the trapped specimen and to provide a detection signal corresponding to the selected modulation frequency, wherein the modulation frequency is associated with a sample vibration based on a sample shape, a sample dimension, and sample elastic properties.

14. The apparatus of claim 13, wherein the control system selects a plurality of modulation frequencies and the detector provides a detection signal corresponding to the plurality of modulation frequencies.

15. The apparatus of claim 14, wherein the control system selects the plurality of modulation frequencies by sweeping the modulation frequency in a frequency range.

16. The apparatus of claim 13, wherein the first optical source and the second optical source are distributed feedback lasers, external cavity semiconductor lasers, or combinations thereof.

17. The apparatus of claim 13, further comprising a trapping optical radiation source that applies a trapping optical beam to the sample, wherein the trapping optical radiation and the vibration inducing optical radiation sources include respective lasers and the control system is coupled so as to select the modulation frequency as a heterodyne frequency between the trapping optical beam and the excitation optical beam.

18. The apparatus of claim 17, further comprising at least one nanohole, wherein the trapping optical beam is directed toward the nanohole so as to trap the specimen at the nanohole.

19. The apparatus of claim 18, wherein the at least one nanohole is a double nanohole.

20. The apparatus of claim 13, wherein the detector is situated to receive at least a portion of the excitation optical beam scattered by the optically trapped specimen.

21. The apparatus of claim 13, wherein the detector is situated to receive at least a portion of the excitation optical beam that is inelastically scattered by the optically trapped specimen.

22. The apparatus of claim 13, wherein the modulation frequency is in a frequency range of between about 10 GHz and 10 THz.

23. An apparatus, comprising:
- an optical fiber having a beam input end and a beam output end, wherein the beam output end includes a beam output surface having a nano-aperture defined thereon;
- a vibration-inducing optical radiation source that delivers an excitation optical beam associated with an excitation frequency to the beam input end of the optical fiber so as to couple the excitation optical beam to an optically trapped specimen to excite a vibrational resonance of the optically trapped specimen under an electrostriction force, wherein the radiation source includes a first source that produces a first optical beam at a first frequency and a second source that produces a second optical beam at a second frequency, wherein the excitation beam includes the first optical beam and the second optical beam such the excitation frequency is a difference frequency between the first frequency and the second frequency; and
- a detection system situated to receive a portion of the excitation optical beam at the excitation frequency from the optically trapped specimen situated at the nano-aperture and associated with specimen vibrations induced by the excitation optical beam.

24. The apparatus of claim 13, wherein the control system is coupled to the optical radiation source so as to sweep the modulated excitation optical beam in a frequency range to excite the vibrational resonance of the optically trapped specimen under the electrostriction force.

25. The apparatus of claim 24, wherein the frequency range is 10 GHz to 10 THz.

* * * * *